United States Patent
Chen et al.

(10) Patent No.: US 12,290,650 B2
(45) Date of Patent: May 6, 2025

(54) SOLUTION PREPARATION DEVICE AND NASAL IRRIGATOR

(71) Applicant: GUANGDONG HORIGEN MOTHER & BABY PRODUCTS CO., LTD., Shantou (CN)

(72) Inventors: Jianbiao Chen, Shantou (CN); Jishun Huang, Shantou (CN); Changxin Chen, Shantou (CN); Yebin Cai, Shantou (CN); Xiaojie Chen, Shantou (CN)

(73) Assignee: Guangdong Horigen Mother & Baby Products Co., LTD., Shantou (CN)

( * ) Notice: Subject to any disclaimer, the term of this patent is extended or adjusted under 35 U.S.C. 154(b) by 0 days.

(21) Appl. No.: 18/815,556

(22) Filed: Aug. 26, 2024

(65) Prior Publication Data

US 2024/0416027 A1    Dec. 19, 2024

Related U.S. Application Data

(63) Continuation-in-part of application No. PCT/CN2023/096046, filed on May 24, 2023.

(30) Foreign Application Priority Data

Mar. 6, 2023   (CN) .......................... 202310250308.0

(51) Int. Cl.
*A61M 3/02*   (2006.01)
(52) U.S. Cl.
CPC ........ *A61M 3/0245* (2013.01); *A61M 3/0202* (2021.05); *A61M 3/022* (2014.02);
(Continued)

(58) Field of Classification Search
CPC ... A61H 35/04; A61H 2033/048; A61M 1/60; A61M 1/71; A61M 2205/36;
(Continued)

(56) References Cited

U.S. PATENT DOCUMENTS

| 4,086,305 | A | * | 4/1978 | Dobritz | ................. | A61M 16/16 |
| | | | | | | 261/36.1 |
| 9,833,380 | B2 | * | 12/2017 | Hoke | .................... | B65D 75/326 |

FOREIGN PATENT DOCUMENTS

| CN | 106890080 A | * | 6/2017 |
| CN | 108721101 A | * | 11/2018 |

(Continued)

*Primary Examiner* — Scott J Medway
(74) *Attorney, Agent, or Firm* — Ming Jiang; OPENPTO US LLC

(57) ABSTRACT

Provided are a solution preparation device and a nasal irrigator. The solution preparation device includes a casing, a flow valve, an on-off valve, a top cover, a first mixer, and a second mixer. A partition is provided in the casing and divides a receiving space into a first chamber and a second chamber. The partition is provided with a mixing channel communicated with the first and second chambers, and a part of the bottom plate corresponding to the second chamber is provided with a discharge channel. The flow valve is arranged in the mixing channel, and the on-off valve is arranged in the discharge channel. Each of the first and second mixers is provided at the top cover, and extends into a respective one of the first and second chambers when the top cover is connected to the casing.

9 Claims, 3 Drawing Sheets

(52) U.S. Cl.
CPC ....... *A61M 3/0258* (2013.01); *A61M 2205/36* (2013.01); *A61M 2209/06* (2013.01); *A61M 2210/0618* (2013.01)

(58) Field of Classification Search
CPC ...... A61M 2209/06; A61M 2210/0618; A61M 3/0202; A61M 3/022; A61M 3/0245; A61M 3/0258; A61M 3/0283; A61M 3/0287; A61M 3/02; A61M 2202/0085; A61M 3/0279; A61M 31/00
See application file for complete search history.

(56) References Cited

FOREIGN PATENT DOCUMENTS

| | | | | | |
|---|---|---|---|---|---|
| CN | 110141493 | A | * | 8/2019 | ............. A61H 35/04 |
| CN | 216365912 | U | * | 4/2022 | |
| CN | 118766747 | A | * | 10/2024 | |
| WO | WO-2013012859 | A1 | * | 1/2013 | ............. A61H 35/04 |

* cited by examiner

SOLUTION PREPARATION DEVICE AND NASAL IRRIGATOR

CROSS-REFERENCE OF RELATED APPLICATION

This application is a continuation-in-part of International Application No. PCT/CN2023/096046, filed May 24, 2023, which claims priority to Chinese Patent Application No. 2023102503080, filed on Mar. 6, 2023, both of which are incorporated herein by reference in their entireties for all purposes.

TECHNICAL FIELD

The disclosure relates to the field of medical devices, particularly to a solution preparation device and a nasal irrigator.

BACKGROUND

A nasal irrigator is primarily used to clear out a foreign matter from the nasal cavity. A flushing-type nasal irrigator typically includes a solution storage container for providing a cleaning solution, a collection container for recovering the cleaning solution, nasal plugs for sealing connection to the user's nostrils, and a vacuum source for creating a relatively negative pressure in the collection container.

In the related art, the nasal irrigator is generally in a one-piece structure. When such nasal irrigator is used in a family or a medical environment, there is an issue of cross-infection if it is shared by multiple users. In addition, the nasal irrigator mainly uses a sodium chloride (NaCl) solution as a cleaning agent. For different users and various clinical symptoms, the concentration of the NaCl solution has to be strictly controlled. For example, for infants and young children, due to their underdeveloped nasal mucosa, the concentration of the NaCl solution used for nasal washing should not be too high, so as to avoid irritation of the nasal mucosa and thus swelling and other symptoms caused therefrom. For adults or those with severe nasal congestion due to acute rhinitis, the concentration of the NaCl solution may be appropriately high. At present, users usually need to purchase special nasal irrigating solution, and the concentration of which is generally fixed. For different usage needs, different concentrations of nasal washing solution has to be purchased, which is costly and very inconvenient for users. Some users choose to prepare the saline solution by themselves, but the concentration of the saline solution cannot be accurately controlled during the preparation process. A too low concentration results in poor nasal washing effects, and a too high concentration would easily cause irritation to the nasal cavity which causes discomfort.

SUMMARY

In view of this, the disclosure provides a solution preparation device and an electric nasal irrigator, which are suitable for use by multiple family members and allows for accurate concentration control over the saline solution.

For this, the disclosure provides the following technical solutions.

In a first aspect, embodiments of the disclosure provide a solution preparation device. The solution preparation device includes a casing, a flow valve, an on-off valve, a top cover, a first mixer, and a second mixer. The casing includes a side wall and a bottom plate, and a receiving space is defined by the side wall and the bottom plate. A partition is provided within the casing, and the partition divides the receiving space into a first chamber and a second chamber. The partition is provided with a mixing channel communicated with each the first chamber and the second chamber. A discharge channel is provided at a part of the bottom plate corresponding to the second chamber. The flow valve is provided in the mixing channel. The on-off valve is provided in the discharge channel. The top cover is detachably connected to the casing. The top cover is configured to close the first chamber and the second chamber. A power interface and a circuit board are provided at the top cover. The power interface is electrically connected with the circuit board and configured to be electrically connected with an external power supply. The circuit board is electrically connected to the flow valve and the on-off valve. The first mixer is provided at the top cover and extends into the first chamber when the top cover is connected to the casing, and the first mixer is electrically connected with the circuit board. The second mixer is provided at the top cover and extends into the second chamber when the top cover is connected to the casing, and the second mixer is electrically connected to the circuit board.

In a second aspect, the embodiments of the disclosure also provide a nasal irrigator. The nasal irrigator includes a handheld handling package, a main unit, and the aforementioned solution preparation device. The handheld handling package has a solution storage part, a connection part, a collection part, and a nasal adapter. The solution storage part has a solution storage cavity. The connection part is located between and communicated with the solution storage part and the collection part. The nasal adapter includes two nasal plugs each being communicated with the solution storage cavity and the collection cavity. The solution preparation device is used to inject a saline solution into the solution storage cavity. The main unit includes an air tube and a cable. The air tube is detachably connected to the collection cavity and is configured to provide a negative pressure to the collection cavity. The cable is detachably connected to the power interface and is configured to power the circuit board.

BRIEF DESCRIPTION OF THE DRAWINGS

In order to more clearly illustrate technical solutions in the embodiments of the disclosure, drawings used in the embodiments will be briefly described below. Apparently, the following drawings are merely some embodiments of the disclosure, and those skilled in the art can obtain other drawings according to these drawings without paying any creative effort.

DETAILED DESCRIPTION OF PREFERRED EMBODIMENTS

The disclosure will be further detailed by means of the embodiments with reference to the drawings. The following embodiments serve to explain the disclosure, and the disclosure is not limited to these embodiments.

Figure 1:
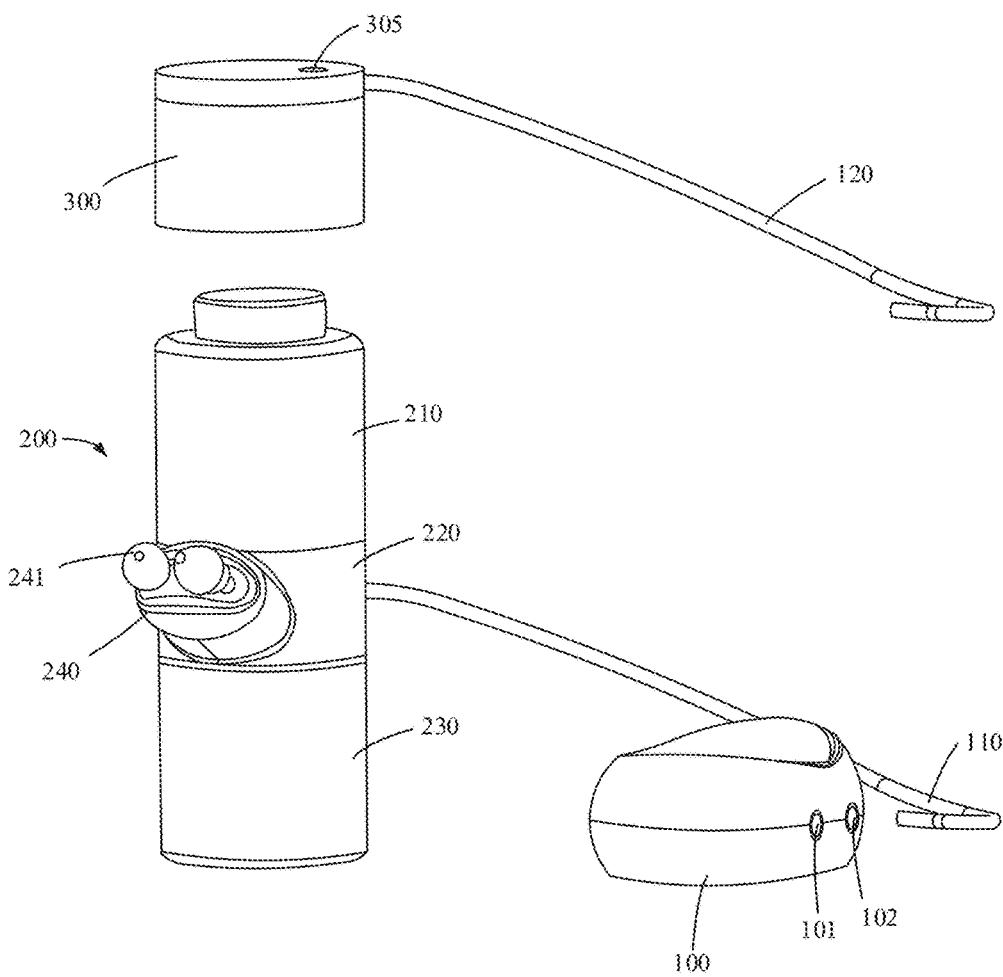
FIG. 1 is a schematic diagram illustrating a structure of a nasal irrigator according to embodiments of the disclosure.

As illustrated in FIG. 1, the embodiments provide a nasal irrigator 10. The nasal irrigator 10 includes a main unit 100, a handheld handling package 200, and a solution preparation device 300, where the main unit 100 is capable of creating a relative negative pressure. The handheld handling package 200, the solution preparation device 300, and the main unit 100 are all independent.

Figure 2:
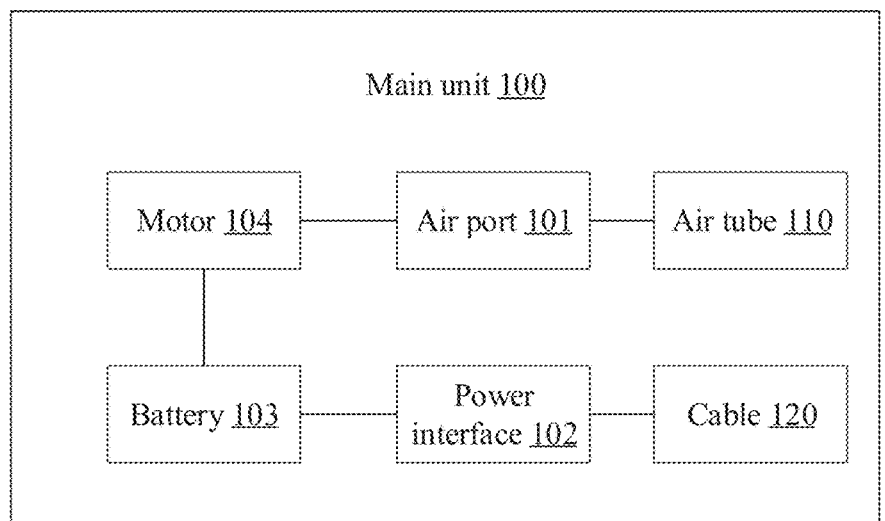
FIG. 2 is a block diagram of a main unit in the nasal irrigator according to the embodiments of the disclosure.

As illustrated in FIG. 1 and FIG. 2, the main unit 100 includes a battery 103, a motor 104, a power interface 102, an air port 101, an air tube 110, and a cable 120. The battery 103 is electrically connected with the motor 104 and is configured to supply power to the motor 104. The motor 104 is connected at the air port 101, and the air port 101 is detachably connected with the air tube 110. When the motor 104 operates, a negative pressure is provided for the air tube 110. The battery 103 is electrically connected with the power interface 102, the power interface 102 may be configured to be electrically connected with one end of the cable 120, and the other end of the cable 120 is configured to be electrically connected with the solution preparation device 300 and power it.

Figure 3:
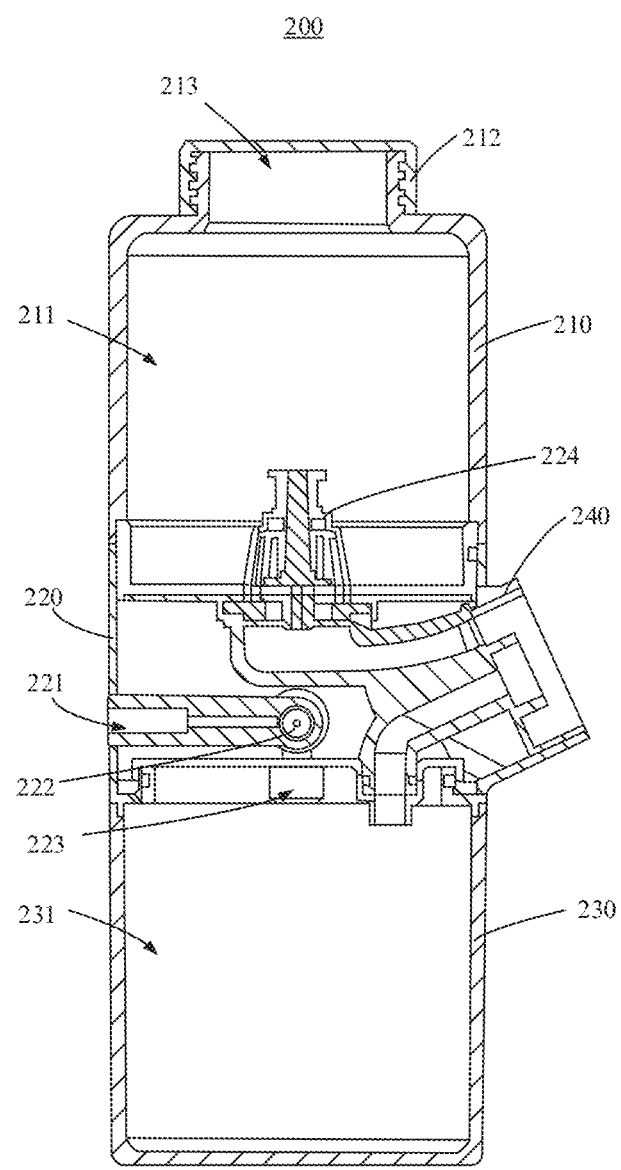
FIG. 3 is a cross-sectional view of a handheld handling package in the nasal irrigator according to the embodiments of the disclosure.

As illustrated in FIG. 3, the handheld handling package 200 has a solution storage part 210, a connection part 220, a collection part 230, and a nasal adapter 240. The solution storage part 210 includes a solution storage cavity 211, and the collection part 230 includes a collection cavity 231. The solution storage part 210 may be substantially located at the top of the handheld handling package 200, and the collection part 230 may be substantially located at the bottom of the handheld handling package 200. The connection part 220 is located between the solution storage part 210 and the collection part 230, and is communicated with both the solution storage cavity 211 and the collection cavity 231. The nasal adapter 240 includes two nasal plugs 241, the two nasal plugs 241 are each communicated with the connection part 220 and are in turn communicated with each of the solution storage cavity 211 and the collection cavity 231.

The solution storage cavity 211 may be located above the connection part 220, and the collection cavity 231 may be located below the connection part. The connection part 220 includes a shell, a top cover, and a base. The top cover is in tight coupling with the solution storage part 210 through a thread structure, and the solution storage cavity 211 is communicated with the connection part. The base is in tight coupling with the collection part 230 through a thread structure, and the collection cavity 231 is communicated with the connection part. The solution storage part 210 of the handheld handling package 200 is also provided with a sealing cover 212, and the sealing cover 212 is provided with internal threads. The solution storage part 210 is provided with an opening 213, and the opening 213 is provided with external threads that match the internal threads of the sealing cover 212. The sealing cover 212 may be in threaded connection with the opening 213 of the solution storage part 210. The sealing cover 212 may be configured to close the opening 213 of the solution storage cavity 211.

The top cover of the connection part 220 is provided with an on-off valve 224, and the on-off valve 224 is used to enable or disable the communication between the solution storage cavity 211 and the connection part 220. The on-off valve 224 may be of any valve structure. The nasal plugs 241 are connected to the on-off valve 224 and thus may be enabled to be communicated with the solution storage cavity 211, and the nasal plugs 241 are also communicated with the collection cavity 231.

The base of the connection part 220 is provided with an air intake tube 221 and a slide switch 222. The base is also provided with a through hole 223 communicated with the collection cavity 231. The slide switch 222 is slidably arranged in the air intake tube 221, and the slide switch 222 may make the through hole 223 opened or closed during the sliding process. The air tube 110 may be detachably plugged into the air intake tube 221 and thus communicated with the air intake tube 221. When the motor 104 in the main unit 100 operates, a negative pressure is provided in the air intake tube 221 through the air tube 110, which in turn drives the slide switch 222 to move to open the through hole 223; at this time, a negative pressure is generated in the collection cavity 231, and the on-off valve 224 is turned on, which allows the saline solution in the solution storage cavity 211 to flow under the negative pressure, pass through the nasal adapters 240, and finally enter the collection cavity 231, thereby completing the nasal washing operation.

There may be multiple handheld handling packages 200. For family use, each family member may use an independent handheld handling package 200, and the corresponding handheld handling package 200 may be used after being connected with the air tube 110. This can avoid cross-infection among family members.

The solution storage cavity 211 holds a saline solution (NaCl solution) during operation. Depending on different users and varying usage requirements, the concentration of the saline solution may vary. If the users prepare the solution by themselves, there is a high likelihood of significant concentration errors. Therefore, in order to meet diverse usage requirements and ensure the precision of the prepared saline solution, the solution preparation device 300 in the embodiments may be utilized to prepare the required saline solution.

Figure 4:
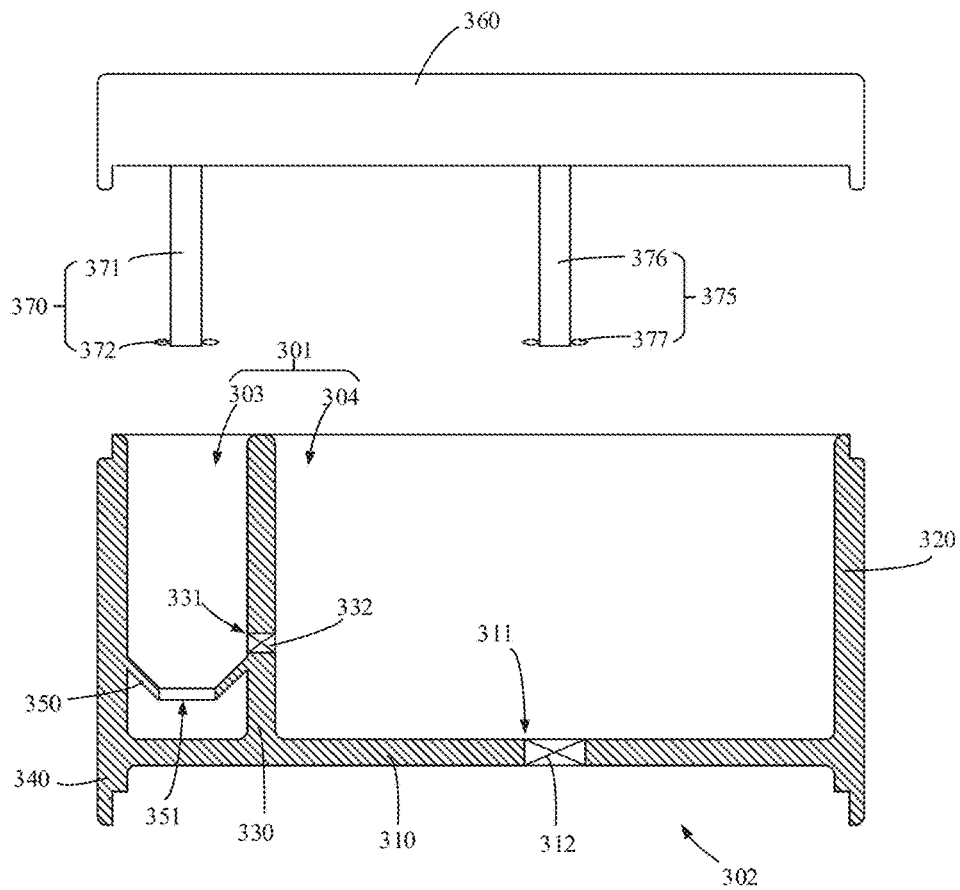
FIG. 4 is a schematic diagram illustrating a structure of a solution preparation device in the nasal irrigator according to the embodiments of the disclosure.
Figure 5:
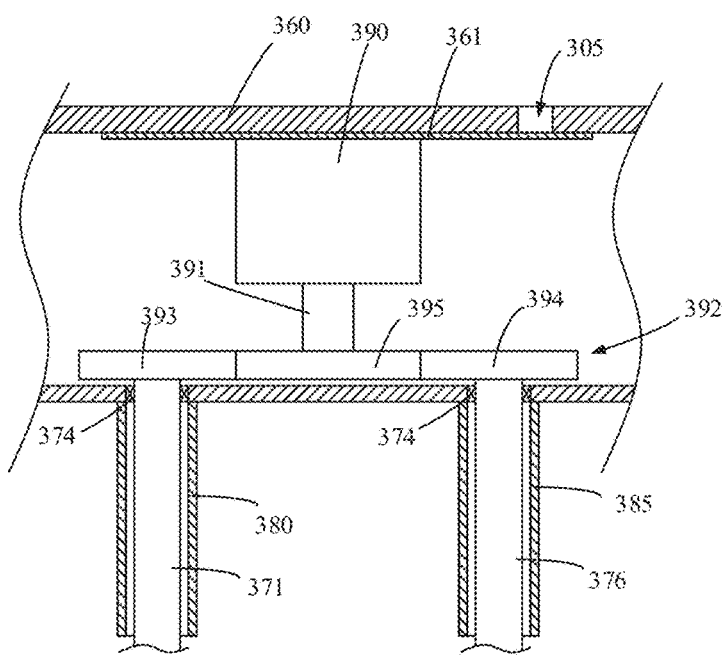
FIG. 5 is a partial cross-sectional view of a top cover in the nasal irrigator according to the embodiments of the disclosure.

As illustrated in FIG. 4 and FIG. 5, the solution preparation device 300 includes a casing 302, a flow valve 332, an on-off valve 312, a top cover 360, a first mixer 370, and a second mixer 375. The casing 302 includes a side wall 320 and a bottom plate 310, and the side wall 320 and the bottom plate 310 enclose a receiving space 301. The receiving space 301 enclosed by the side wall 320 and the bottom plate 310 may be in any form, such as circular, rectangular, or polygonal, which is not limited in the embodiments.

A partition 330 is provided in the casing 302, and the partition 330 divides the receiving space 301 into a first chamber 303 and a second chamber 304. The first chamber 303 and the second chamber 304 are isolated from each other. The partition 330 is provided with a mixing channel 331 communicated with each of the first chamber 303 and the second chamber 304. Through the mixing channel 331, the solution in the first chamber 303 may flow into the second chamber 304, and the liquid in the second chamber 304 may flow into the first chamber 303. A discharge channel 311 is provided in a part of the bottom plate 310 corresponding to the second chamber 304. The discharge channel 311 runs through the bottom plate 310, and is configured to discharge the solution from the second chamber 304. The volume of the second chamber 304 is significantly larger than that of the first chamber 303. In an implementation, the volume of the first chamber 303 is less than or equal to 10% of the volume of the second chamber 304. Of course, in other implementations, the volume ratio of the first chamber 303 to the second chamber 304 may also be other values.

The first chamber 303 may be configured to prepare a high-concentration saline solution (NaCl solution), such as a saturated saline solution, while the second chamber 304 may be configured to dilute the high-concentration saline solution. The flow valve 332 is provided in the mixing channel 331, and is used to control the mixing channel 331 to be opened or closed. The flow valve 332 may also control the flow rate of the liquid passing through the mixing channel 331. The on-off valve 312 is provided in the discharge channel 311, and is used to control the discharge channel 311 to be opened or closed.

The top cover 360 is detachably connected with the casing 302, and may be used to seal the first chamber 303 and the second chamber 304. As illustrated in FIG. 5, the top cover 360 is provided with a power interface 305 and a circuit board 361. The power interface 305 is electrically connected with the circuit board 361, and is used to be connected with an external power supply. The power interface 305 may be connected with the cable 120, so as to be electrically connected with the main unit 100; and then, the battery 103 of the main unit 100 may power the power interface 305. The circuit board 361 is electrically connected with the flow valve 332 and the on-off valve 312. The circuit board 361 integrates thereon a processor and a memory, the memory may store control instructions, and the processor may call the control instructions to control the flow valve 332 to be opened or closed, control the flow rate of the liquid passing through the mixing channel 331, and control the on-off valve 312 to be opened or closed.

The first mixer 370 is provided at the top cover 360, and extends into the first chamber 303 when the top cover 360 is covered on the casing 302. The first mixer 370 is electrically connected to the circuit board 361, and used to stir the solution in the first chamber 303. The processor may control the first mixer 370 to start or stop working, and may also control the rotation speed of the first fixer 370. The second mixer 375 is provided at the top cover 360, and extends into the second chamber 304 when the top cover 360 is covered on the casing 302. The second mixer 375 is electrically connected to the circuit board 361, and used to stir the solution in the second chamber 304. The processor may control the second mixer 375 to start or stop working, and may also control the rotation speed of the second mixer 375.

As illustrated in FIG. 4 and FIG. 5, the first mixer 370 includes a first rotation shaft 371 and paddles 372 mounted at an end of the first rotation shaft 371. The second mixer 375 includes a second rotation shaft 376 and paddles 377 mounted at an end of the second rotation shaft 376. The first rotation shaft 371 and the second rotation shaft 376 are substantially parallel to each other. In some embodiments, the solution preparation device 300 further includes a motor 390 and a transmission mechanism 392. The motor 390 is provided on the top cover 360 and is electrically connected with the circuit board 361. The processor on the circuit board 361 controls the motor 390 to start or stop working. The motor 390 is in transmission cooperation with the transmission mechanism 392, and is used to drive the first rotation shaft 371 or the second rotation shaft 376 to rotate. To save costs, there may be only one motor 390, which drives the first rotation shaft 371 and the second rotation shaft 376 to rotate synchronously. Specifically, the transmission mechanism 392 includes a first gear 393, a second gear 394, and a third gear 395. The first gear 393 is mounted on the first rotation shaft 371, the second gear 394 is mounted on the second rotation shaft 376, and the third gear 395 is mounted on the output shaft of the motor 390 and is engaged with each of the first gear 393 and the second gear 394. When the motor 390 works, the first rotation shaft 371 and the second rotation shaft 376 are rotated simultaneously.

During the solution preparation, the user may add an excess amount of salt (NaCl) to the first chamber 303, and then add water thereto. Thereafter, the motor 390 is started, the first mixer 370 stirs the solution in the first chamber 303, to cause the salt to be dissolved in the water, thereby obtaining a saturated saline solution. At room temperature, the concentration of the saturated saline solution is fixed. At this time, the flow valve 332 is opened, and the saturated saline solution flows into the second chamber 304. By controlling the flow valve 332, the volume of saturated saline solution entering the second chamber 304 may be regulated. Then, water is added to the second chamber 304 for volume adjustment, to reach a fixed total volume. As such, the saline concentration of the diluted solution in the second chamber 304 can be precisely controlled.

For example, the concentration of the saturated saline solution in the first chamber 303 is "a", the volume of the saturated saline solution added into the second chamber 304 is "b", and the final volume after volume adjustment in the second chamber 304 is "c". Then, the concentration of the diluted saline solution in the second chamber 304 is (a*b)/c. Therefore, based on the required concentration of the saline solution, it only need to control the volume of the saturated saline solution added to the second chamber 304. To further improve the accuracy of the saline concentration of the diluted solution, the entire process may be automatically controlled by the processor. The solution preparation device 300 may also include a human-machine interaction module (not shown), which is used to receive users' commands. The human-machine interaction module may be one or more buttons, displays, etc., provided on the top cover 360, which is not limited here. The human-machine interaction module is electrically connected with the circuit board 361, and the user may input the desired concentration of the saline solution. The processor may automatically calculate, based on the user's command, the volume of the saturated saline solution needed to be added to the second chamber 304.

Furthermore, the second chamber 304 may also be provided with a volume indicator line. When operating manually, the user may simply add the water up to the volume indicator line during volume adjustment, which reduces the difficulty of operation for the user.

The solubility of salt in water is related to temperature, and fluctuations in temperature may cause changes in the saline concentration of the saturated saline solution. Therefore, to further improve the accuracy, the solution preparation device 300 also includes a first heater 380. The first heater 380 is provided at the top cover 360, and extends into the first chamber 303 when the top cover 360 is covered on the casing 302, and configured to heat the solution in the first chamber 303. The first heater 380 is electrically connected with the circuit board 361. The first heater 380 may be configured to heat the solution to a fixed temperature, such as 40° C. The water temperature at 40° C. is moderate for the human body, and is less likely to cause irritation during subsequent nasal washing. In addition, at 40° C., the solubility of salt in water is high, and less saturated saline solution is needed in the subsequent dilution process, which allows one prepared saturated saline solution to be diluted into multiple saline solutions required.

During the nasal washing process, the temperature of the nasal washing solution should not be too high or too low, and it is appropriate to be between 38° C.-42° C. Therefore, the diluted saline solution also needs to be heated to the appropriate temperature. In the embodiments, the solution preparation device 300 also includes a second heater 385. The second heater 385 is provided at the top cover 360, and extends into the second chamber 304 when the top cover 360 is covered on the casing 302. The second heater 385 is electrically connected with the circuit board 361. The second heater 385 is configured to heat the solution in the second chamber 304. In an implementation, the second heater 385 may be configured to heat the solution in the second chamber 304 to 40° C.

The first heater 380 and the second heater 385 may be any heating elements, which is not limited in the embodiments. In some embodiments, both the first heater 380 and the second heater 385 are hollow heating tubes. The first rotation shaft 371 is assembled on the top cover 360 through a bearing 374 and passes through the hollow space of the first heater 380. The second rotation shaft 376 is assembled on the top cover 360 through a bearing 374, and passes through the hollow space of the second heater 385. This arrangement facilitates the layout of various components and saves space.

Since the solution in the first chamber 303 is supersaturated, the first chamber 303 contains undissolved solid salt particles. When the flow valve 332 is opened, these salt particles may flow into the second chamber 304 with the solution. During the subsequent dilution process, these salt particles are dissolved, causing the saline concentration of the diluted solution to be significantly higher than the required concentration of the saline solution, this would result in errors. Therefore, these salt particles need to be prevented from entering the second chamber 304.

In some embodiments, a ring baffle 350 is provided in the first chamber 303. The ring baffle 350 is connected between the side wall 320 and the partition 330, and there is a spacing between the ring baffle 350 and the bottom plate 310. The ring baffle 350 is provided with an opening 351, and the opening 351 may be located in the center of the ring baffle 350 and run through the ring baffle 350. The mixing channel 331 is located above the ring baffle 350. During the stirring process of the first mixer 370, the undissolved salt particles would be in a suspended state in the first chamber 303. After the first mixer 370 stops stirring, the salt particles would gradually be deposited downward, pass through the opening 351, and be finally accumulated on the bottom plate 310. When the flow valve 332 is opened, the baffle 350 may prevent the salt particles from entering the second chamber 304.

Furthermore, the ring baffle 350 may be inclined towards the bottom plate 310, and thus be substantially in a funnel shape, with the opening 351 located at the center of the ring baffle 350. This arrangement allows the salt particles deposited on the ring baffle 350 to slide towards the bottom plate 310, falling into the space between the ring baffle 350 and the bottom plate 310. When the flow valve 332 is opened, the salt particles are blocked by the ring baffle 350, and prevented from entering the second chamber 304. When the user adds salt to the first chamber 303, he/she may control the added salt to just reach the opening 351 of the ring baffle 350, and then water may be added for mixing and stirring. In order to ensure the supersaturated state of the solution in the first chamber 303, the mixing channel 331 and the ring baffle 350 may be arranged at relatively high positions to ensure that the amount of added salt can meet the supersaturation requirement. For example, in an implementation, the mixing channel 331 may be arranged in the middle area of the partition 330.

The solution preparation device 300 provided in the embodiments may be used as follows. The user first adds an excess amount of salt to the first chamber 303, then adds water to the first chamber 303, makes the top cover 360 covered on the casing 302, and starts the first mixer 370 and the first heater 380 for stirring and mixing, thereby obtaining a saturated saline solution. Then, the flow valve 332 is opened, and a predetermined amount of saturated saline solution is fed into the second chamber 304. Thereafter, the user opens the top cover 360, and adds water to the second chamber 304 to until a standard volume is reached. Then, the second mixer 375 is started until well mixed, and the second heater 385 is started heat the solution to a predetermined temperature. When in use, the on-off valve 312 is opened to add the diluted saline solution to the solution storage cavity 211 of the handheld handling package 200 for use.

In some implementations, to further simplify the user's operation, a program following the above preparation method may be preset in advance, and a button may be provided on the top cover 360. When the button is triggered, the program runs to cause the above operations to be executed. In some another implementations, a prompt tone/message may also be set, and when user participation is required during running of the program, the user may be prompted by the prompt tone/message to proceed to a next operation.

The above solution preparation device 300 may configure saline solutions of different concentrations according to the needs of different users, which is suitable for use by multiple family members.

To facilitate the user in releasing the prepared saline solution into the solution storage cavity 211, an edge of the bottom plate 310 is provided with a fixing part 340. The fixing part 340 extends away from the side wall 320, and the fixing part 340 is provided with internal threads cooperating with the external threads of the solution storage part 210. When there is a need to release the prepared saline solution into the solution storage cavity 211, the user simply connects the fixing part 340 of the solution preparation device 300 to the solution storage part 210 through the threads, and then opens the valve 312, which is convenient for the user to operate.

With the solution preparation device 300 provided in the embodiments, a supersaturated saline solution is first prepared in the first chamber 303, and a pre-calculated amount of saturated saline solution is fed into the second chamber 304, and then the volume of the solution in the second chamber is adjusted to a fixed volume, thereby obtaining a saline solution of the required concentration. During the preparation process, the user only needs to add an excess amount of salt and an appropriate amount of water to the first chamber 303, and adjusts the volume of the solution in the second chamber 304 to a standard volume. This allows for the preparation of a saline solution of precise concentration required, without need for the user to accurately measure the weight of the salt and the volume of water. This simplifies the user's operation and improves the accuracy of the prepared saline solution, and it is suitable for use by multiple family members.

The nasal irrigator 10 integrating the above solution preparation device 300 is suitable for use by multiple family members, which prevents cross-infection among the members, and can meet the nasal washing needs of different users.

In this description, the specific features or characteristics described may be combined in any one or more embodiments or examples in an appropriate manner. Moreover, unless contradictory, those skilled in the art may combine the different embodiments or examples described in this description, as well as the characteristics of different embodiments or examples described in this description. Finally, it should be noted that the above examples are only used to illustrate the technical solutions of the disclosure rather than limiting it. Although a detailed description of the disclosure has been given with reference to the above embodiments, those skilled in the art should understand that they can still modify the technical solutions described in the above examples, or equivalently replace some technical features therein; and these modifications or replacements do not deviate from the essence and scope of the technical solutions of the above embodiments of the disclosure.

What is claimed is:

1. A nasal irrigator, comprising:
   a handheld handling package, wherein the handheld handling package comprises a solution storage part, a connection part, a collection part, and a nasal adapter, the solution storage part comprises a solution storage cavity, the connection part is located between and communicated with the solution storage part and the collection part, the nasal adapter comprises two nasal plugs, and each of the nasal plugs is communicated with the solution storage cavity and the collection cavity; and
   a solution preparation device, wherein the solution preparation device is configured to inject a saline solution into the solution storage cavity, and the solution preparation device comprises:
   a casing, wherein the casing comprises a side wall and a bottom plate, a receiving space is defined by the side wall and the bottom plate; a partition is provided within the casing, the partition divides the receiving space into a first chamber and a second chamber, the partition is provided with a mixing channel communicated with each the first chamber and the second chamber; and a discharge channel is provided at a part of the bottom plate corresponding to the second chamber;
   a flow valve, provided in the mixing channel;
   an on-off valve, provided in the discharge channel;
   a top cover detachably connected to the casing, wherein the top cover is configured to close the first chamber and the second chamber, a power interface and a circuit board are provided at the top cover, the power interface is electrically connected with the circuit board, and the circuit board is electrically connected to the flow valve and the on-off valve;
   a first mixer, wherein the first mixer is provided at the top cover and extends into the first chamber when the top cover is connected to the casing, and the first mixer is electrically connected with the circuit board; and
   a second mixer, wherein the second mixer is provided at the top cover and extends into the second chamber when the top cover is connected to the casing, and the second mixer is electrically connected to the circuit board; and
   a main unit, wherein the main unit comprises an air tube and a cable, the air tube is detachably connected to the connection part and configured to provide a negative pressure to the collection cavity, the cable is detachably connected to the power interface and configured to power the circuit board.

2. The nasal irrigator of claim 1, wherein the solution storage cavity is provided at a top of the handheld handling package, the top of the handheld handling package is provided with a sealing cover for closing the solution storage cavity, the sealing cover is provided with internal threads, and the handheld handling package is provided with external threads cooperating with the internal threads.

3. The nasal irrigator of claim 1, wherein the solution preparation device further comprises a first heater and a second heater, the first heater is provided at the top cover and extends into the first chamber when the top cover is connected to the casing, the second heater is provided at the top cover and extends into the second chamber when the top cover is connected to the casing, and the first heater and the second heater are electrically connected with the circuit board.

4. The nasal irrigator of claim 3, wherein each of the first heater and the second heater is a hollow heating tube; the first mixer comprises a first rotation shaft and paddles installed at an end of the first rotation shaft, the first rotation shaft passes through the first heater; the second mixer comprises a second rotation shaft and paddles installed at an end of the second rotation shaft, and the second rotation shaft passes through the second heater.

5. The nasal irrigator of claim 4, wherein the solution preparation device further comprises a motor and a transmission mechanism, the motor is provided at the top cover and electrically connected with the circuit board, the motor is configured to cooperate with the transmission mechanism to drive the first rotation shaft or the second rotation shaft to rotate.

6. The nasal irrigator of claim 5, wherein the transmission mechanism comprises a first gear, a second gear, and a third gear, the first gear is mounted on the first rotation shaft, the second gear is mounted on the second rotation shaft, and the third gear is mounted on an output shaft of the motor and engaged with the first gear and the second gear.

7. The nasal irrigator of claim 1, wherein a ring baffle is provided in the first chamber, the ring baffle is provided between the side wall and the partition, the ring baffle is spaced from the bottom plate, an opening is provided in the ring baffle, and the mixing channel is located above the ring baffle.

8. The nasal irrigator of claim 7, wherein the ring baffle is inclined towards the bottom plate.

9. The nasal irrigator of claim 1, wherein a fixing part is provided at an edge of the bottom plate, the fixing part extends away from the side wall, and the fixing part is provided with internal threads.

* * * * *